United States Patent [19]

Rosenberg

[11] Patent Number: 6,083,920

[45] Date of Patent: Jul. 4, 2000

[54] COMPOSITIONS FOR MODULATING INTRACELLULAR INOSITOL TRISPHOSPHATE CONCENTRATION

[75] Inventor: Abraham Rosenberg, Avondale Estates, Ga.

[73] Assignee: Ayurcore, Inc., San Jose, Calif.

[21] Appl. No.: 08/771,047

[22] Filed: Dec. 20, 1996

Related U.S. Application Data

[60] Provisional application No. 60/009,007, Dec. 21, 1995.

[51] Int. Cl.⁷ .......................... A01N 43/04; A01N 57/00
[52] U.S. Cl. ............................................. 514/25; 514/114
[58] Field of Search ........................................ 514/25, 114

[56] References Cited

U.S. PATENT DOCUMENTS

| | | | |
|---|---|---|---|
| 4,940,694 | 7/1990 | Della Valle et al. | 514/25 |
| 5,128,332 | 7/1992 | Siren et al. | 514/103 |
| 5,190,925 | 3/1993 | della Valle et al. | 514/25 |
| 5,321,012 | 6/1994 | Mayer et al. | 514/25 |
| 5,556,843 | 9/1996 | Romero et al. | 514/114 |
| 5,654,281 | 8/1997 | Mayer et al. | 514/25 |
| 5,677,285 | 10/1997 | Romeo et al. | 514/28 |

FOREIGN PATENT DOCUMENTS

WO 94/07507  4/1994  WIPO .

OTHER PUBLICATIONS

Berridge, Inositol trisphosphate and calcium signalling, *Nature*, 361:315–325, 1993.

Burger and van Meer, Sphingolipid trafficking–sorted out?, *Trends in Cell Biology*, 2:332–337, 1992.

Choi and Rothman, The Role of Glutamate Neurotoxicity in Hypoxic–ischemic Neuronal Death, *Annu. Rev. Neurosci.*, 13:171–82, 1990.

Copani et al., Activation of Metabotropic Glutamate Receptors Prevents Neuronal Apoptosis in Culture, *Journal of Neurochemistry*, 64:101–108, 1995.

Desai and Conn., Selective activation of phosphoinositide hydrolysis by a rigid analogue of glutamate, *Neuroscience Letters*, 109:157–162, 1990.

Grove and Maestro, Prevention of the TPA–Mediated Down–Regulation of Protein Kinase C, *Biochemical and Biophysical Research Communications*, 151:94–99, 1988.

Hannum et al., Ceramide: Intracellular signal for apoptosis, *Trends in Biochemical Sciences*, 20:73–77, 1987.

Hartmann et al., β–Amyloid Protein Amplifies Calcium Signalling in Central Neurons From the Adult Mouse, *Biochemical and Biophysical Research Communications*, 194:1261–1220, 1993.

Kolesnick, Sphingomyelinase Action Inhibits Phorbol Ester–induced Differentiation of Human Promyelocytic Leukemic (HL–60) Cells, *J. Biological Chemistry*, 264:7617–7623, 1989.

Leli and Hauser, Chlorpromazine induces accumulation of Inositol Phosphates in C6 Glioma Cells, *Biochemical and Biophysical Research Communications*, 135:465–472, 1986.

Li and Jope, Inhibition of Receptor–Coupled Phosphoinositide Hydrolysis by Sulfur–Containing Amino . . . , *Biochemical Pharmacology*, 38:2781–2787, 1989.

Linnik et al., Evidence Supporting a Role for Programmed Cell Death in Focal Cerebral Ischemia in Rats, *Stroke*, 24:2002–2009, 1993.

Matesic et al., Microtubule–Associated Protein 2 as an Early Indicator of Ischemia–Induced Neurodegeneration in the Gerbil Forebrain, *J. Neurochemistry*, 63:1012–1020, 1994.

Michel and Agid, Death of Septal Cholinergic Neurons Produced by Chronic Exposure to Glutamute Is Prevented by the Noncompetitive NMDA . . . , *J. Neuroscience Research*, 40:764–775, 1995.

Nozowa et al., Novel Procedure for Measuring Psychosine Derivatives by an HPLC Method, *J. Neurochemistry*, 59:607–609, 1992.

Porter et al., L–Aspartate–β–hydroxamate exhibits mixed agonist/antagonist activity at the glutamate . . . , *Neuro-Science Letters*, 144:87–89, 1992.

Ritchie et al., Regulation of Phosphoinositide Hydrolysis in Cultured Astrocytes by Sphingosine and Psychosine, *Biochemical and Biophysical Research Communications*, 186:790–795, 1992.

Rosenberg et al., Developmental Patterns of Ganglioside Sialosylation Coincident with Neuritogenesis in Cultured Embryonic Chick Brain Neurons, *J. Biological Chemistry*, 267:10607–10612, 1992.

Schwarzmann and Sandhoff, Complex Carbohydrates, *Meth. Enzymol.*, 138:319–341, 1987.

Thomsen et al., (S)–4–Carboxy–3–Hydroxphenylglycine, an Antagonist of Metabotropic Glutamate Receptor (mGluR)1a and an Agonist of . . . , *J. Neurochemistry*, 62:2492–2495, 1994.

Tiziano et al., Intracerebral 1S,3R–1–aminocyclopentane–1, 3–dicarboxylic acid . . . , *Neuroscience Letters*, 162:12–16, 1993.

Watkins et al., Structure–activity relationships in the development of excitatory amino acid receptor agonists and . . . , *Trends in Pharmacological Sciences*, 11:25–33, 1990.

Clementi et al., Nitric Oxide Modulation of Agonist–Evoked Intracellular . . . , American Society for Pharmacology and Experimental Therapeutics, 47:517–524, 1995.

Helmeste et al., Serotonin Uptake Inhibitors Modulate Intracellular . . . , European Journal of Pharmacology, Molecular Pharmacology Section 288:373–377, 1995.

Ortmann et al., Ovarian Steroids Modulate Gonadotropin–releasing Harmone–induced Biphasic . . . , J. Steroid Biochem. Molec. Biol., 54:101–109, 1995.

*Primary Examiner*—Theodore J. Criares
*Attorney, Agent, or Firm*—Fish & Richardson P.C.

[57] ABSTRACT

Compositions and methods for the modulation of aberrant inositol trisphosphate concentration in neurons is disclosed. Inositol trisphosphate stimulates an increase in intraneuronal calcium ion concentration which can, if unregulated, lead to acute neurotoxicities following such insults as brain seizures, and brain anoxia/ischemia; and lead to chronic neurotoxicities in such diseases as Alzheimer's disease, Huntington's disease, Parkinson's Disease, and amyotrophic lateral sclerosis. Inhibited inositol trisphosphate production results in aberrantly low calcium ion levels leading to neuronal apoptosis.

7 Claims, 11 Drawing Sheets

Sphingosine   Lysosphingomyelin   Lysocerebroside (psychosine)

COMPOSITIONS FOR MODULATING INTRACELLULAR INOSITOL TRISPHOSPHATE CONCENTRATION

This application claims benefit from provisional application 60/009,007, filed Dec. 21, 1995.

BACKGROUND OF THE INVENTION

This invention relates to modulation of inositol trisphosphate ($InsP_3$) concentration in neurons.

Within the nervous system, information is conveyed from one neuron to another by electrical signals that are generated by the flux of ions, including calcium ions, across the neuronal cell membrane. When certain cell surface receptors are bound, calcium enters the cell through selective channels and may also be released from intracellular stores. The cell surface receptors involved include those that are bound by excitatory amino acids such as glutamate. Glutamate, and other agonists (discussed below), bind metabotropic receptors that are coupled to G proteins, and thereby instigate the biochemical cascade that leads to the release of calcium from intracellular stores.

There are seven immunologically distinct subtypes of metabotropic glutamate receptors (M1–M7). When bound, two of these receptor subtypes, M1 and M5, produce the second messenger $InsP_3$ by stimulating phosphoinositide-specific phospholipase C (hereinafter, "phospholipase C"), which converts phosphatidylinositol bisphosphate, a lipid located in the plasma membrane, to diacylglycerol and $InsP_3$ (this reaction is illustrated in FIG. 1).

In addition to L-glutamate, metabotropic receptors are activated by L-aspartate and by the pharmacological agonists quisqualate, ibotenate, and trans-ACPD (trans-(+-1)-1-amino-1,3-cyclopentanedicarboxylate; Schoepp et al., supra). L-aspartate and aspartate analogs also act as agonists for metabotropic receptors expressed by neurons in the brain (Porter et al., Neurosci. Lett., 144:87–89, 1992). In addition to stimulating metabotropic receptors, quisqualate and ibotenate stimulate jonotropic receptors, which are coupled to ion channels (Watkins et al., Trends Pharmacolo. Sci. 11:25–33, 1993). Thus, of the excitatory amino acid receptor agonists, trans-ACPD may be more selective for phosphoinositide-linked metabotropic receptors (Desai and Conn, Neurosci. Lett., 109:157–162, 1990). Pharmacological testing has also shown that L-trans-pyrrolidine-2,4-dicarboxylate and D,L-homocysteate stimulate receptor-coupled phosphoinositide hydrolysis in rat brain tissue (Li and Jope, Biochem. Pharmacol. 38:2781–2787, 1989).

Overstimulation of metabotropic receptors is thought to occur in the course of several neurological disorders. This overstimulation, and the resulting increase in $InsP_3$ production, increases intracellular calcium to levels that produce severe hyper-functional defects (see, for example, Thomsen et al., J. Neurochem., 62:2492–2495, 1994) and eventual neurotoxicity and death (Berridge, Nature, 361:315–325, 1993; Choi and Rothman, Ann. Rev. Neurosci., 13:171–182, 1990). Specific disorders associated with overstimulation of metabotropic glutamate receptors in the brain include limbic seizures (Tiziano et al., Neurosci. Lett., 162:12–16, 1993) and chronic neurodegenerative disorders such as Alzheimer's disease, Huntington's disease, Parkinson's Disease, and amyotrophic lateral sclerosis (ALS; more commonly known as Lou Gehrig's Disease).

Another type of neuronal cell death, referred to as programmed cell death or apoptosis, may be affected by reduced activity of metabotropic glutamate receptors (Copani et al., J. Neurochem. 64:101–108, 1995). Similarly, inhibition of $InsP_3$ is thought to mediate neuronal apoptosis by reducing intracellular calcium.

SUMMARY OF THE INVENTION

The work described herein is aimed at altering the mechanism(s) that regulate the concentration of $InsP_3$ in order to treat neurological disorders that are associated with hyperactive function and neuronal cell death. Accordingly, the present invention provides methods and compositions for modulating the concentration of InsP3 in neurons. Disorders associated with glutamate excitotoxicity (either directly or indirectly) should be particularly amenable to treatment with these compositions and methods.

DETAILED DESCRIPTION

Figure 1:
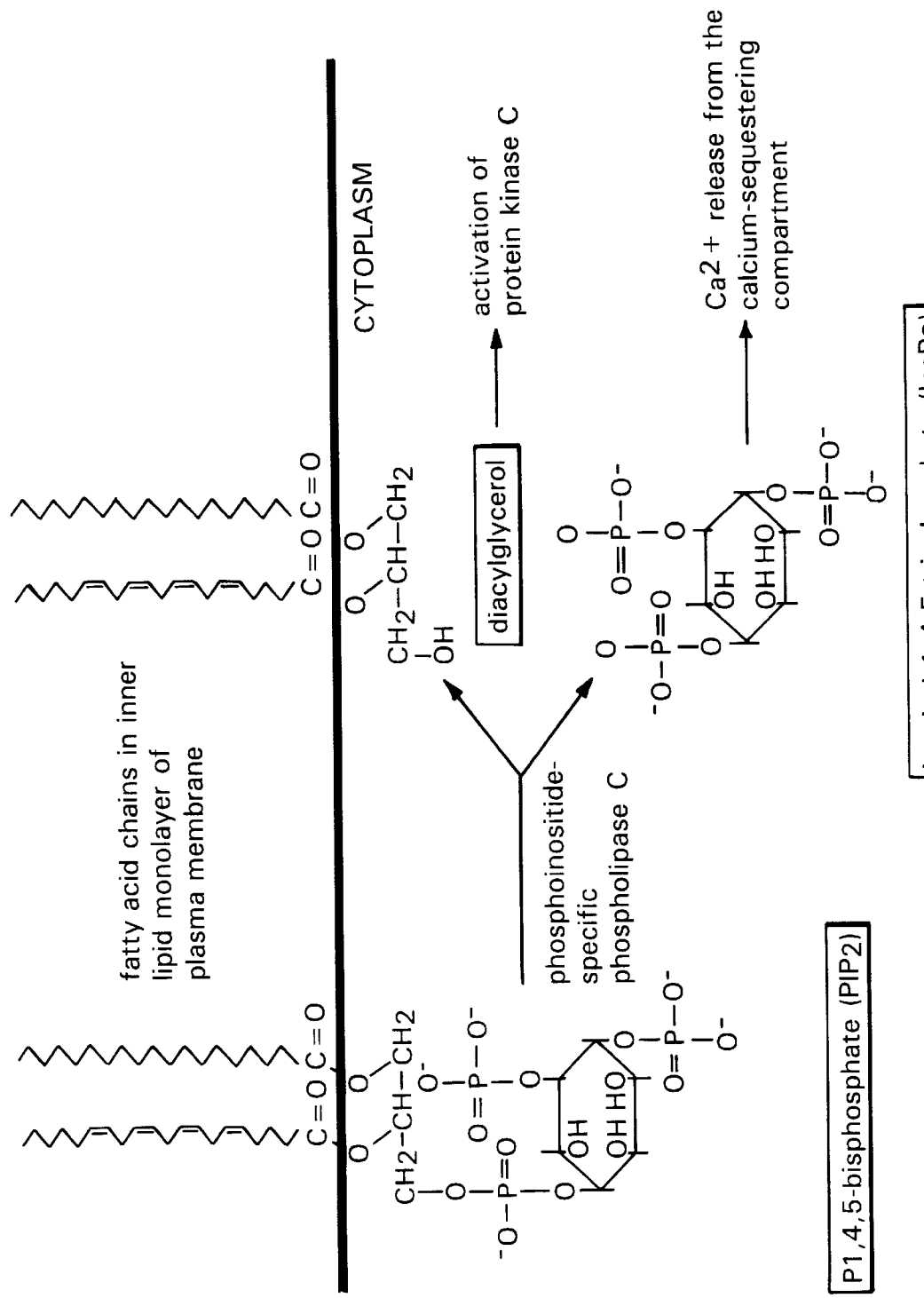
FIG. 1 is a diagram illustrating conversion of phosphitidyl inositol 4,5,-bisphosphate ($PIP_2$) into diacylglycerol and inositol trisphosphate ($InsP_3$).
Figure 2:
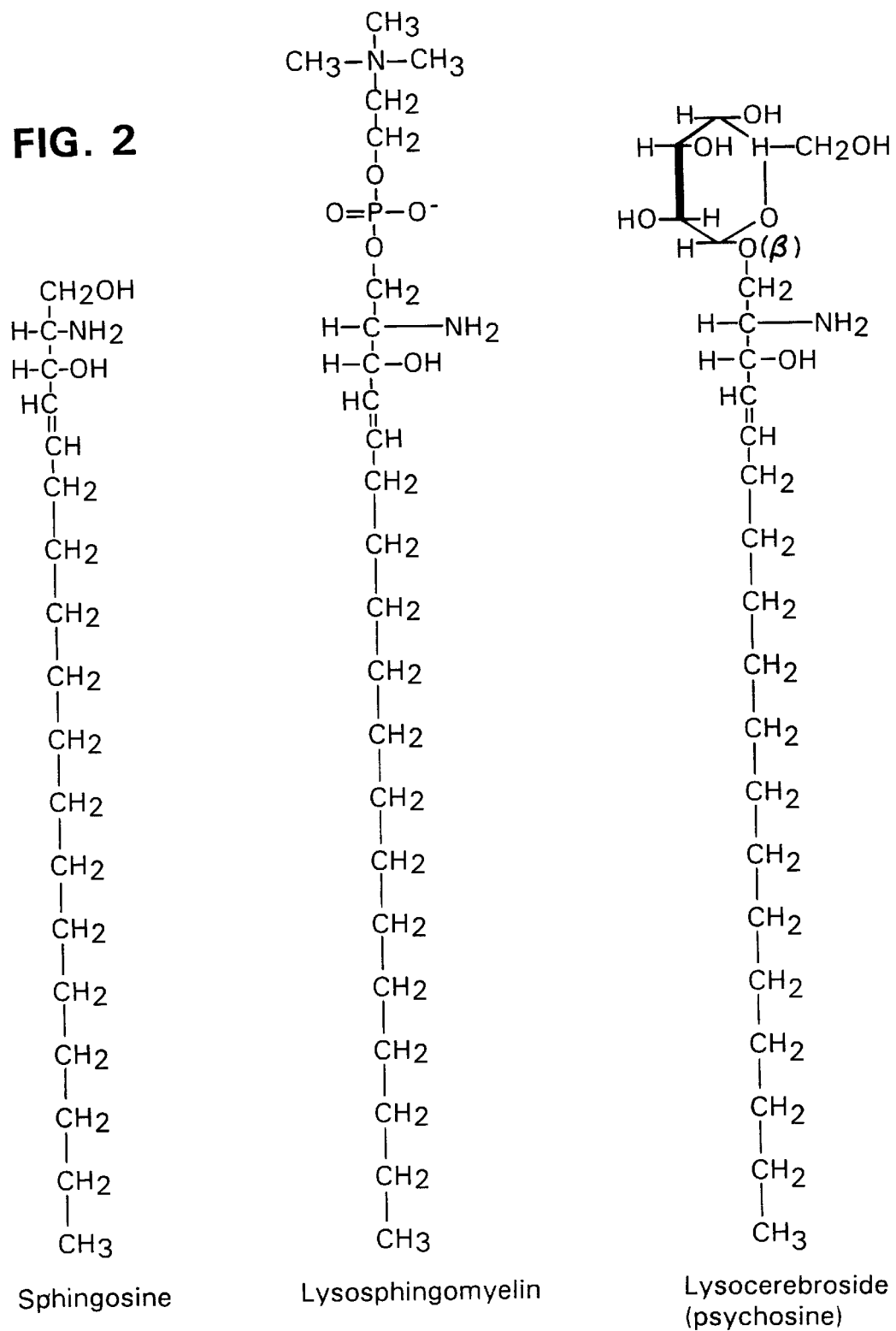
FIG. 2 is a diagram of the structure of the (lyso) sphingolipids sphingosine, lysosphingomyelin, and lysocerebroside.

Sphingolipid is the name given to derivatives of fatty acid-containing compounds of the long chain amphiphilic amino alcohol sphingosine whose terminal hydroxyl group is substituted by phosphoryl, glycosyl, or other groups. Cationic sphingolipids that lack the fatty acid component of the parent sphingolipid compound are called lysosphingolipids. Free unsubstituted sphingosine and the terminally substituted derivatives of sphingosine: lysosphingomyelin (sphingosyl phosphoryicholine), lysocerebroside (also called glycosyl sphingosine or psychosine), lysosulphatides, and lysogangliosides are all lysosphingolipids.

It is disclosed herein that, at non-toxic physiological levels, naturally occurring sphingosine increases the production of $InsP_3$ in brain neurons, while naturally occurring lysosphingolipids, lysocerebroside, and lysosphingomyelin (and no other naturally occurring lysosphingolipids) potently repress $InsP_3$. It is further disclosed that lysosphingomyelin and lysocerebroside potently and specifically repress the increase in $InsP_3$ that is induced when neurons are exposed to excitatory amino acids or their analogue agonists, such as ibotenate and quisqualate. The repression of $InsP_3$ by lysosphingomyelin and lysocerebroside competes with the stimulation of $InsP_3$ by sphingosine.

The invention provides a method of modulating $InsP_3$ concentration in a neuronal cell of a mammal that has, or is suspected of having, a disorder associated with an abnormal concentration of $InsP_3$. The method involves administering to the mammal a composition containing an isolated compound that modulates the concentration of $InsP_3$ by acting downstream from a cell surface receptor, and a pharmaceutically acceptable carrier. The modulation produced by this method may result in a decrease in $InsP_3$ production (as can be caused by the compounds lysocerebroside or lysosphingomyelin) or an increase in $InsP_3$ production (as can be caused by the compound sphingosine). The carrier may consist of an excipient including buffers such as citrate buffer, phosphate buffer, acetate buffer, and bicarbonate buffer, amino acids, urea, alcohols, ascorbic acid, phospholipids, proteins such as serum albumin, gelatin, EDTA, sodium chloride, liposomes, polyvinylpyrollidone, mannitol, sorbitol, glycerol, propylene glycol, and polyethylene glycol (e.g., PEG-4000 or PEG-8000). The neuron that is contacted may reside within the peripheral nervous system or the central nervous system. Preferably, the neuron is within the brain.

The composition described above may be administered by any route known to skilled pharmacologists. The route of administration may be, for example, intra-arterial, intracerebral, intrapulmonary, or transmucosal. Preferably, administration is by subcutaneous, intramuscular, or intraperitoneal injection and, most preferably, by intravenous injection. If necessary, the compounds of the invention, or compounds discovered by the method of the invention, can be modified to increase the efficiency with which they cross the blood brain barrier. In order to enable these compounds to penetrate the blood brain barrier, they can be delivered in encapsulated cell implants (e.g., those produced by CytoTherapeutics, Inc., Providence RI; see Bioworld Today 7:6, Dec. 2, 1996). Delivery of drugs to the brain may also be accomplished using RMP-7™ technology (Alkermes, Inc., Cambridge, Mass: see Business Wire, "Third Major Agreement for Prolease Sustained Release Drug Delivery System," (Dec. 2, 1996) or implantable wafers containing the drug (see PR Newswire, "Implantable Wafer is First Treatment to Deliver Chemotherapy Directly to Tumor Site," Sep. 24, 1996). The compositions may also be administered using an implantable pump for direct aministration into intrathecal fluid (e.g., that made by Medtronic, Minneapolis, Minn; see Genetic Engineering News, "Neurobiotechnology Companies Focus Programs on Pain and Neuroprotection," Nov. 1, 1996).

The route of administration and the amount of protein delivered will be determined by factors that are well within the ability of skilled artisans to assess. Furthermore, skilled artisans are aware that the route of administration and dosage of a therapeutic substance may be varied for a given patient until a therapeutic dosage level is obtained. The dosage and length of any treatment are known to depend on the nature and severity of the disease and to vary from patient to patient as a function of age, weight, sex, and general health, as well as the particular compound to be administered, the time and route of administration and other drugs being administered concurrently. Skilled artisans will be guided in their determination of the appropriate therapeutic regime by, e.g., Gregoriadis (*Drug Carriers in Biology and Medicine*, Academic Press) and Goodman and Gilman (*The Pharmacological Basis of Therapeutics*, 6th Edition). Skilled artisans can be guided further in their determination of the correct therapeutic dosage by assessing behavioral criteria, as disclosed in Example VIII, or by performing any standard test of a patient's cognitive or motor skills. Typically, the dosage of an $InsP_3$ modulatory substance described herein will range from 0.01 to 100 mg/kg of body weight. More preferably, sphingolipids such as sphingosine, lysosphingomyelin, and lysocerebroside are administered in the range from about 0.5 mg/kg body weight to 1.5 mg/kg body weight for each compound. It is expected that regularly repeated doses of the $InsP_3$ modulatory compound will be necessary over the life of the patient. Alternatively, a neuron may be contacted in vitro.

A pharmaceutical composition containing a compound that modulates $InsP_3$ in mammalian neuronal tissue and a pharmaceutically acceptable carrier is another embodiment of the invention. This composition can modulate the concentration of $InsP_3$ by either increasing or decreasing the concentration of $InsP_3$ within a neuron, such as a neuron within the brain, to a concentration that is sufficient to treat a disorder that is associated with abnormal $InsP_3$ production.

When an increase in intracellular $InsP_3$ is sought, the isolated compound of the invention is a lysosphingolipid which may be, but is not limited to, sphingosine. When a decrease in intracellular $InsP_3$ is sought, the isolated compound of the invention is a lysosphingolipid which may be, but is not limited to, lysosphingomyelin or lysocerebroside. Preferably, the mechanism by which the composition of the invention modulates inositol trisphosphate concentration is by modulating the activity of phosphoinositidase-specific phospholipase C. The composition can be used to modulate $InsP_3$ in a neuron in vitro or in vivo.

When the invention provides a composition containing a lysosphingolipid in a pharmaceutically acceptable carrier, the lysosphingolipid is preferably characterized as being the D-erythro isomer and having: (1) a trans-4 double bond, (2) a net positive charge, (3) an aliphatic chain of 8 or more carbon atoms linked in series, and (4) a net neutrally charged substituent on the oxygen atom of carbon atom 1. The substituent may be, but is not limited to, any of the following: hydrogen, monosaccharide, disaccharide, trisaccharide, polysaccharide, phosphorylcholine, and phosphoryl ethanolamine. Preferably, agents fitting these parameters and occurring at physiological, ng/mg protein levels (Kolesnick, J. Biol. Chem., 264:7617, 1989), are the naturally occurring lysosphingolipids sphingosine, psychosine, and lysosphingomyelin. Saturation of the double bond of sphingosine by hydrogenation produces the compound sphinganine which has less than one third the membrane insertion potential of sphingosine. Compounds such as N-acetyl sphingosine or ceramide, in which the amino group is amidated and rendered non-ionic, apparently have little or no physiological effect in this system. A cationic free base, 4-trans-enic amphiphile provides physiological activity. Tonically neutral 1-0-substitution provides inhibitory activity.

A method of identifying a compound that modulates the production of $InsP_3$, preferably in a neuron, is also provided by the invention. In this method, a neuron is contacted, either in vitro or in vivo with a compound and inositol, such as tritium-labeled inositol, under conditions sufficient to modulate $InsP_3$ production. The amont of inositol trisphosphate produced is then measured. Any change in the concentration of $InsP_3$ can be measured by standard techniques known to one of ordinary skill in the art. For example, one can monitor the amount of radiolabelled InsP3 produced from prelabelled inositol starting material. Alternatively, symptoms of a mammal having a neural disorder can be monitored. The compound identified by this method of the invention may modulate an increase or a decrease in $InsP_3$ production. The method of identifying a compound that modulates neuronal inositol trisphosphate concentration may also include contacting the neuron with a second compound that modulates $InsP_3$.

The invention also provides for a first and a second compound contacting a neuron under conditions sufficient to modulate $InsP_3$ production.

In addition to neurons, the nervous system contains neuroglia, such as astrocytes, Schwann cells, and microglia, which contribute to repair processes in the nervous system and lend support to the neurons. Neuroglia and neurons are phenotypically distinct cell types. For example, astrocytes have major adrenergic (rather than excitatory amino acid) metabotropic receptors and, in these cells, $InsP_3$ production is enhanced by sphingosine and inhibited by psychosine (Ritchie et al., Biochem. Biophys. Res. Commun., 186:790–795, 1992). In addition, the way in which $InsP_3$ controls calcium ion concentration and signalling in astrocytes is distinctly different from that in brain neurons: in astrocytes, sphingolipid modulation of $InsP_3$ production occurs by α-adrenergic stimulation of ITP production via a G protein intermediate that is inhibited by treatment with pertussis toxin (Ritchie et al., supra). Furthermore, $InsP_3$ produced in astrocytes is communicated through gap junctions to other cells, whereas in neurons, $InsP_3$ remains within the cell where it modulates the concentration of $Ca^{2+}$.

Applicants have shown that sphingosine increases the basal level of InsP3 in brain neurons independently of stimulation of excitatory amino acid receptors by any agonists (the effect of sphingosine being downstream from the receptors). Because the excitatory amino acid analogues are structurally and functionally unrelated to sphingolipids (as reflected by their action at a distinct point in the signalling pathway), these analogues do not predict the present invention.

The drug chlorpromazine (10-(3-dimethylaminopropyl)-2-chlorphenothiazine) raises the level of $InsP_3$ in rat C6 glioma cells (Leli and Hauser, Biochem. Biophys. Res. Commun., 135:465–472, 1986). However, chlorpromazine is unrelated structurally and functionally to the sphingolipid compositions of the present invention, and therefore does not predict the present invention.

Sphingosine and several sphingosine derivatives inhibit a protein kinase C isoform that is activated by diacylglycerol and phorbol esters in non-neuronal cell types such as lymphocytes, neutrophils, granulocytes, Chinese hamster ovary cells, and platelets. (Hannum and Bell, Trends Biochem. Sci., 20:73–77, 1987; and Grove and Maestro, Biochem. Biophys. Res. Commun., 151:94–99, 1988). However, it is disclosed herein that the effects of sphingosine on brain neurons are independent of protein kinase C inhibition: the protein kinase C inhibitor staurosporine does not influence the effects of sphingosine, lysocerebroside, or lysosphingomyelin on $InsP_3$ production in brain neurons that are responsive to excitatory amino acids. As a result, the protein kinase C-mediated pathway and the phospholipase C-mediated pathway for controlling intraneuronal calcium ion concentration are independent. Consequently, compounds that affect the protein kinase C pathway are not predictive of the effects of compounds, such as the sphingolipids of the present invention, on phospholipase C pathway regulation.

A synthetic analog of the amino acid glycine ((S)-4-carboxy-3-hydroxyphenyl glycine) blocks a metabotropic (but not ionotropic) amino acid receptor and is thereby thought to render protection against seizures (Thomsen et al., supra). However, blockage of glutamate-responsive metabotropic receptors by therapeutic glutamate antagonists is highly impractical because these antagonists are generally toxic (Michel and Agid, J. Neurosci. Res., 40:764–775, 1995). In contrast, the compositions and methods of this invention contain naturally occurring lysosphingolipids that act downstream from the cell surface receptor. These substances are associated with a reduced risk of toxicity.

It is a significant advantage of the invention that naturally occurring compounds within a non-toxic physiologic range are used, limiting the possible dangers to the patient and undesirable side effects that accompany treatment with non-natural, synthetic pharmaceutical compounds. The lysophingolipids are metabolized and cannot accumulate to dangerous levels in patients, as is the case for the synthetic receptor blockers. Also, the lysosphingolipids used herein do not rely upon liver detoxification and kidney excretion so their use will have minimal risk of liver or kidney damage. In addition, receptor blockage disturbs normal brain function, which may be avoided by targeting phospholipase C and allowing receptor function to regulate neuronal ion balance. A further advantage of the invention is that the naturally occurring compounds of the invention are readily available, making use of the present invention potentially much less expensive to the patient than the use of synthetic pharmaceutical preparations.

An object of the invention is to provide methods and compositions that can be used to treat mammalian conditions associated with glutamate excitotoxity. These conditions include, but are not limited to, acute conditions stemming from brain anoxia or ischemia, brain seizure activity, and chronic conditions such as Alzheimer's disease, Parkinson's Disease, Huntington's disease, and amyotrophic lateral sclerosis.

Other features and advantages of the invention will be apparent from the following detailed description, and from the claims. Although methods and materials similar or equivalent to those described herein can be used in the practice or testing of the invention, the preferred methods and materials are described below.

The finding that lysosphingolipids influence $InsP_3$ production which, in turn, controls the concentration of calcium ions in neurons, led to the compositions and methods described herein for controlling aberrant $InsP_3$ production in various neuronal disorders. Exemplary, non-limiting compositions and methods that can be used to carry out the invention are described below.

EXAMPLE 1

Preparation of Neuronal Cell Cultures

Primary cultures of neurons were prepared from the telencephalon of white Leghorn chick embryos on the eighth day of their development (Rosenberg et al., J.Biol. Chem. 267:10601–10612, 1992). The neurons were seeded in 24-well plastic tissue culture plates that had been coated with L-polylysine. The density of the neurons was $10_5$ cells per well, and they were cultured in Dulbecco's modified Eagle's medium/Ham's high glucose F-12 medium (1:1, vol:vol) containing 500 ng/L sodium selenite, 500 μg/L transferrin, and 165 pmole/L EGF. The cultures were maintained at 37° C. under 5% $CO_2$ in air for 4 days, by which time the cells had differentiated into neurite-bearing cortical granulocytic neurons. These cultures of mature embryonic neurons were used for phosphoinositide hydrolysis assays (as described in Example 2).

PC12 cells, from a rat adrenal pheochromocytoma cell line, were used as a model of neurons from the peripheral nervous system. These cells were obtained from a common laboratory cell culture stock and grown in plastic culture flasks in Dulbecco's modified Eagle's medium (DMEM) supplemented with 5% heat-inactivated horse serum and 10% heat-inactivated fetal calf serum (PC12 cells are also available from the American Type Culture Collection under the Accession number CRL 1721). The cells were grown at 37° C. in 5% $CO_2$ in air until a confluent monolayer formed. The cells were dispersed into 24-well plastic tissue culture plates at a density of $10_5$ cells per well and used for the phosphoinositide hydrolysis assays (as described in EXAMPLE 2).

EXAMPLE 2

Measurement of Inositol Trisphosnhate Production by a Phosphoinositide Hydrolysis Assay Receptor-stimulated and basal unstimulated hydrolysis of phosphoinositides was measured by the following procedure. In order to label the cellular phosphoinositides metabolically, the primary cultures of chick cortical neurons (described in Example 1) were incubated overnight with 0.5 ml Dulbecco's modified Eagle's medium containing 1 $\mu$Ci [$^3$H]myo-inositol per well. The cells were then washed twice with 1 ml Dulbecco's phosphate-buffered saline (PBS) and 0.5 ml of PBS containing 4.5 g/L glucose was added. Sphingosine, psychosine, lysosulphatide, or lysosphingomyelin, prepared as the hydrochloride salt dissolved in water, were then added to produce the desired extracellular concentration in specific wells, and the 24-well plates were swirled gently on a rotary shaker for 1 hr at 23° C. The cells were then washed twice with 1 ml PBS, and pre-incubated for 15 minutes at 37° C. with 0.5 ml PBS containing 10 mM LiCl and the compound to be tested was added. After 30 minutes, the experiment was terminated by adding 1 ml of ice-cold methanol to each well and transferring the material in each well to polypropylene tubes that contained 0.4 ml water and 1 ml chloroform. The tubes were vortexed thoroughly, then centrifuged at 500×g for 5 minutes to separate the aqueous and chloroform phases. For each sample, a 1.5-ml aliquot of the upper (aqueous) phase was applied to a small column containing BioRad AG1X8 resin (formate form). Free [$^3$H]inositol and [$^3$H] glycerophosphoinositol were washed through the column with 5 ml of a solution containing 5 mM sodium borate and 60 mM sodium formate. The total phosphorylated [$^3$H] inositol fraction was eluted from the column for radiometric scintillation spectrometry analysis with 3 ml 1.0 M ammonium formate/0.1 M formic acid;

In addition, a 0.5 ml aliquot of the lower (chloroform) phase of each sample was analyzed radiometrically by scintillation spectrometry in order to determine the quantity of lipid-bound [$^3$H]myo-inositol. Estimation of phosphoinositide hydrolysis by phospholipase C is based upon the quantity of [$^3$H]inositol phosphates produced, and is expressed as the percentage of the latter relative to total free and componential [$^3$H]inositol (dpm ammonium formate+ dpm chloroform fractions).

EXAMPLE 3

$InsP_3$ Production in Neurons

A. Inositol trisphosphate production in PC12 Cells

Figure 3:
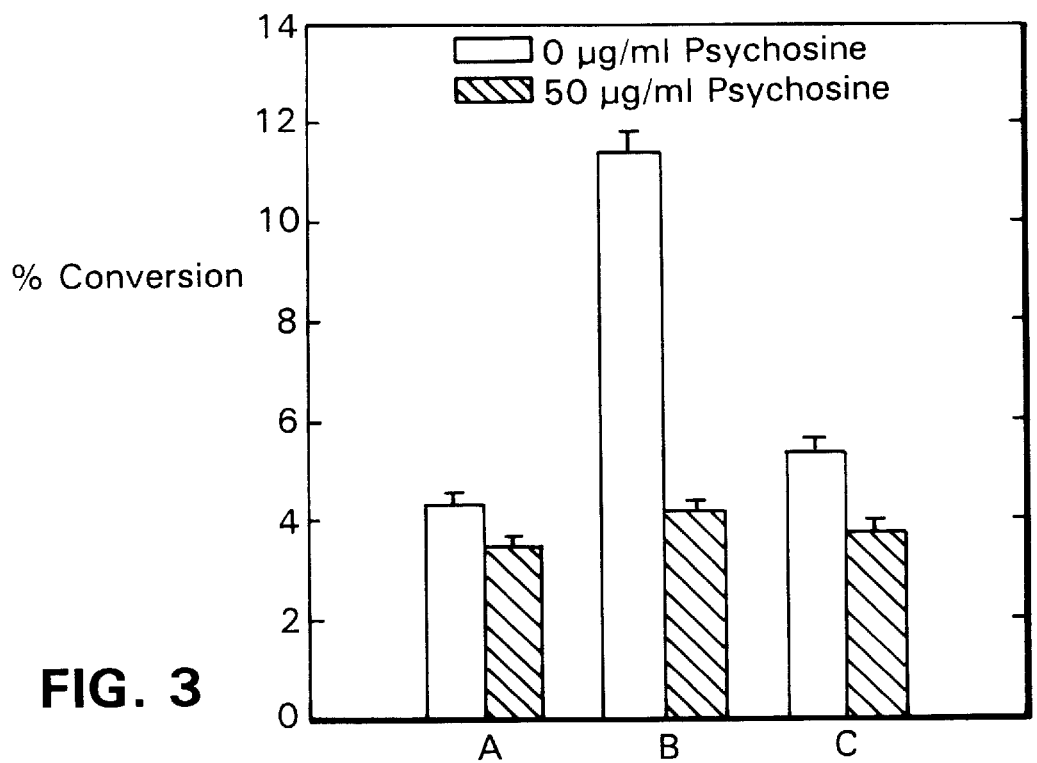
FIG. 3 is a bar graph illustrating the effects of sphingosine and psychosine (lysocerebroside) on basal and bradykinin-stimulated phosphoinositide signalling in PC-12 cells. The bars marked A represent cells that were untreated. The bars marked B represent cells that were exposed to 10 $\mu$M bradykinin for 30 minutes. The bars marked C represent cells that were exposed to 100 $\mu$g/ml sphingosine for 30 minutes before treatment with an excitotoxic agent.

PC12 cells display a strong phospholipase C-linked metabotropic receptor response to bradykinin, an effective pain producing agonist. As with the other neuronal cells, sphingosine tonically upregulated the basal, unstimulated level of $InsP_3$ production in PC12 cells. Psychosine and lysosphingomyelin strongly inhibit $InsP_3$ production in PC12 cells and, even at relatively moderate levels, can entirely block the sensitivity of PC12 cells to bradykinin. These findings are shown in FIG. 3.

Figure 4:
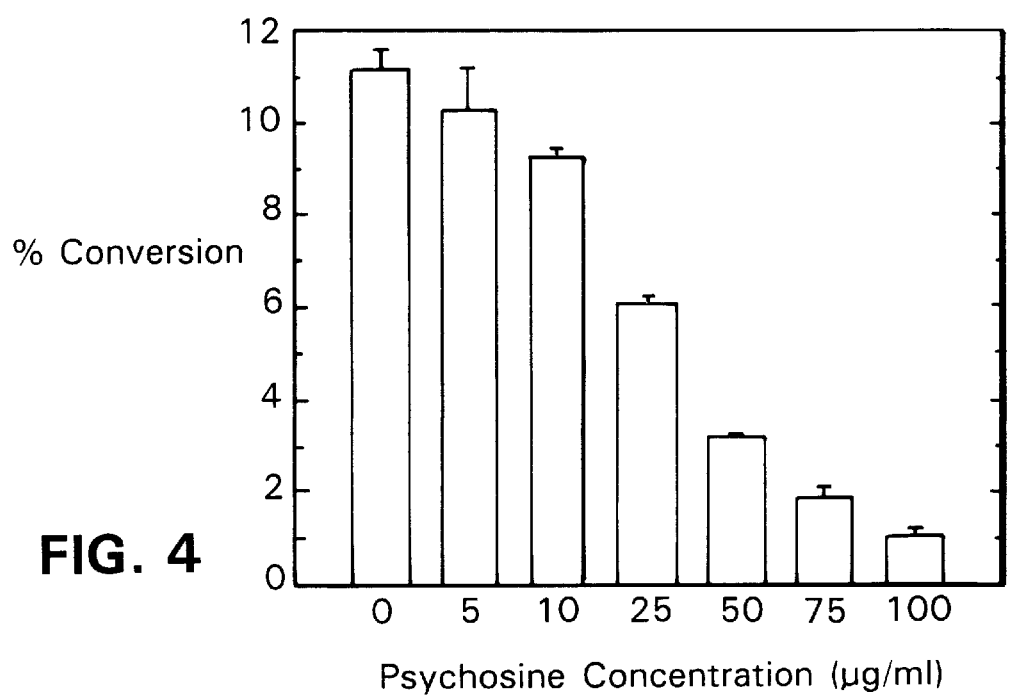
FIG. 4 is a graphical representation of the concentration effects of psychosine repression of bradykinin-stimulated phosphoinositide signalling in PC12 cells.

The degree of $InsP_3$ inhibition is a function of the log of the psychosine concentration for a fixed time of exposure (FIG. 4). Exposing PC12 cells to 50 $\mu$M exogenous psychosine for 30 minutes was sufficient to reduce a metabotropic response to 10 $\mu$M bradykinin to half maximum.

B. $InsP_3$ Production in Cultured Neurons

Cultured primary chick cortical neurons that were prelabeled with [$^3$H]myo-inositol were examined for enhanced $InsP_3$ signalling in response to various agonists including glutamate, aspartate, and the metabotropic M1/M5 receptor agonists ibotenate and quisqualate. As shown in Table 1, sphingosine, lysocerebroside, and lysosphingomyelin potently modulated $InsP_3$ signalling. Lysosulphatide was without inhibitory effect in this system. Thus, sphingosine tonically enhanced the basal, unstimulated $InsP_3$ level in cortical neurons, while psychosine and lysosphingomyelin blocked this enhancement whether it was caused by sphingosine or by metabotropic glutamate receptor agonists.

TABLE 1

| | | Lysosphinogolipid Modulator | | | |
|---|---|---|---|---|---|
| Agonist[a] | Ins-P-n[b] | Psy[c] | Lsm:Sph[d] | Lsm[c] | Psy:Sph[d] |
| Aspartate | 2.70 ± 0.06[f] | 1.00 ± 0.06[e] | 2.00 ± 0.05[f] | 1.00 ± 0.06[f] | 2.65 ± 0.50[f] |
| Ibotenate | 3.00 ± 0.10[f] | " | 2.10 ± 0.10[f] | " | 3.10 ± 0.35[f] |
| Quisquilate | 3.00 ± 0.05[f] | " | 2.25 ± 0.15[f] | " | 3.30 ± 0.25[f] |
| Glutamate | 3.30 ± 0.05[f] | " | 3.00 ± 0.10[f] | " | 3.00 ± 0.35[f] |

[a]100 $\mu$M agonist, 20 min.
[b]Values calculated from % PtdIns-P-n splitting and normalized to control value (3.50 ± 0.02% = 1.00).
[c]Neurons preincubated with 20 $\mu$M Psychosine or 20 $\mu$M Lysosphingomyelin for 30 min., washed with PBS, and treated with agonist.
[d]20 $\mu$M Psychosine + 20 $\mu$M Sphingosine, 20 $\mu$M Lysosphingomyelin + 20 $\mu$M Sphingosine.
[e]Compared with no-agonist controls by Student's t-test, p = 0.5.
[f]p < $10^{-5}$ (n = 9).

EXAMPLE 4

Monitoring Lysosphingolipid Content of Neurons

Agonist-binding to metabotropic receptors influences the levels of lysosphingolipid in neuronal membranes.

However, there is no convenient methodology available for the measurement of lysosphingolipid content in cultured neurons. As a result, a sensitive method of fluorometric tracing has been devised and is described herein. The measurement of lysosphingolipid content in cultured neurons is based on the stable fluorescence-tagging procedure using 4-fluoro, 7-nitrobenzofuran (NBDZF) described by Nozowa et al J. Neurochem. 59:607–609, 1992). The procedure was applied to: resting neurons; neurons exposed to 100 $\mu$M metabotropic receptor agonist for 1 hour; resting neurons exogenously enriched in lysosphingolipids; and neurons exogenously enriched in lysosphingolipids and exposed to metabotropic receptor agonist for 1 hour. The neurons were scraped in batches of $10_7$ (1 Petri dish, approximately 8 cm in diameter, is equivalent to 2 mg membrane protein) and subjected to anaylsis.

Total lipids were removed from the neuron samples by repeated extraction with chloroforn:methanol (2:1, vol:vol). The lysosphingolipids were separated from total neuronal lipid in 90±5% recovery yield (n=10) by the stepped chromatographic procedure of Van Veldhoven et al. (Anal. Biochem. 183:177–189, 1989). The recovered lysosphingolipids were stably tagged with NBDZF by the rapid procedure of Nozowa et al. (supra). The fluorescence tagged neuronal lysosphingolipids were separated in parallel with reference standards NBDZF-Sph, NBDZF-Psy, and NBDZF-Lsm on high performance silica gel thin layer chromatography plates with acetonitrile:$H_2O$ (10:0.5, vol:vol). The highly fluorescent, well separated bands were scraped from the plate. The fluorescence tagged lysosphingolipids are eluted from the scraped silica gel with methanol:1 N HCl (1:0.02, vol:vol). The fluorescence tagged lysosphingolipid eluates were quantitated against reference standards by fluorescence measurement in a Perkin-Elmer LS-5 Fluorescence Spectrometer.

Resting, unstimulated neurons contained 113±13 pmoles sphingosine, 50±10 pmoles lysocerebroside, and 5±0.2 pmoles lysosphingomyelin per mg protein (n=9). Neurons stimulated with L-glutamate agonist, e.g. 100 $\mu$M ibotenate for 1 hour contained 85±3 pmoles sphingosine, 80±5 pmoles lysocerebroside and 52±2 pmoles lysosphingomyelin per mg protein (n=6). It appears that a compensatory increase in the inhibitory lysosphingolipids may occur during extended exposure to agonist. Sphingosine is convertible in the cytoplasmic face of cis-Golgi (Burger and DeMeer, Trends Cell Biol., 2:332–337, 1992) to lysocerebroside by transfer of a glucosyl moiety from UDP-glucose to the 1-0-position of sphingosine by the action of glucosyltransferase:lysocerebroside (psychosine) synthase (Schwarzmann and Sandhoff, Methods in Enzymology, 138:319–341, 1987). An analogous system exists for lysosphingomyelin synthesis by transfer of a phosphorylcholine moiety from CDP-choline.

Neurons synthesize prodigious amounts of sphingolipids with 92 mass % of the total cellular sphingolipid located in the outer lipid bilayer of the plasma membrane. Sialoglycosphingolipids are present at the level of 40.8±1.9 $\mu$g/mg cell protein, and sphingomyelin is present at 12.1±3.0 $\mu$g per mg cell protein.

Sphingolipid content of neurons exposed to sphingosine, lysocerebroside, and lysosphingomyelin was examined as follows. A Petri dish containing approximately $10_7$ neurons was incubated with 5 $\mu$Ci [$^3$H]myo-Ins in 3 ml DMEM overnight to prelabel the phosphoinositide $InsP_3$ may contain. The neurons were washed with PBS and 3 ml of PBS containing 4.5 g/l glucose was added. Preparations of sphingosine, lysocerebroside, lysosphingomyelin (Sigma Chemical Co., St. Louis, Mo.) and combinations of each were prepared as the hydrochloride salt dissolved in PBS. The lysosphingolipids were added to the Petri dishes to produce a concentration ranging from 0–150 $\mu$M. The dishes were held at room temperature for 0.5, 1, or 2 hours, then washed with PBS and incubated with 5 Units of trypsin in glucose/PBS for 4 hours at 37° C. Trypsinization removes non-specifically bound lysosphingolipids that may adhere to extracellular plasma membrane protein domain s. Non-specific adherence between cationic micelles of lysosphingolipids and the neuronal glycocatyx avoided by performing the experiments with lysosphingolipid concentrations below the critical micelle concentration. Neurons were analyzed for lysosphingolipid content as described above.

Following expo sure to 50 $\mu$M sphingosine for 1 hour, the content of sphingosine in the neurons was 430±70 pmoles/mg protein (n=9). Following exposure to 50 $\mu$M lysocerebroside, the content of sphingosine was 220±45 pmoles/mg protein (n=20), and exposure to 50 $\mu$M lysosphingomyelin resulted in 105±0.15 pmoles sphingosine/mg, protein (n=9).

EXAMPLE 5

Monitoring Metabotropic Receptor Function

Metabotropic receptor function was examined in intact neurons by assaying lysosphingolipid modulation of calcium ion signalling. Approximately $1\times10^6$ cortical neurons were cultured on rectangular L-polylysine-coated coverslips and loaded with lysocerebroside or lysosphingomyelin to a level of 150±20 pmoles per mg protein. The neurons were returned to complete Ham's high glucose medium/DMEM (1:1, vol:vol) and infiltrated with 5 $\mu$M fura 2/AM (Molecular Probes, Eugene, Oreg.). Fura 2 is a calcium chelator whose fluorescence absorbance shifts to shorter wavelength upon calcium ion binding is measurable in intact cells. A change in intraneuronal calcium ion concentration was monitored as a change in the fluorescence spectrum.

The neurons were exposed to 10 $\mu$M glutamate agonist (for example, ibotenate) for 30 minutes at 37° C. The coverslips were then transferred to quartz cuvettes in medium containing 250 $\mu$M sulfinpyrazone to prevent fura 2/AM diffusion. Fluorescence ratios were recorded in a Perkin-Elmer LS-5 Fluorescence Spectrometer thermostatted at 37° C. at excitation wavelengths of 340 and 380 nm, a nd emission measurement at 500 nm. Calcium ion signalling in agonist-stimulated neurons was 3.0±0.2 arbitrary units for ibotenate-exposed neurons. In lysosphingomyelin and lysocerebroside-loaded neurons, agonists elicited no calcium signalling measurably over controls, indicating that agonist activity can be effectively blocked by inhibitory lysosphingolipids.

EXAMPLE 6

Monitonring Phospholipase C Activity in the Presence of Lysosphingolipids

A. Monitoring free Phospholipase C Activity in Solution

The effects of sphingosine, lysocerebroside, and lysosphingomyelin on the kinetics of pure, immunologically isolated phospholipase C isoforms beta, delta, and gamma (which are commercially available) was examined. For each isoform, 10 $\mu$M sphingosine was added to a reaction medium consisting of 1 $\mu$g phospholipase C isoform/ml, Tris-malate buffer (50 mM, pH 7.0) containing 100 $\mu$M phosphatidyl inositol bis-phosphate tri-ammonium salt, 0.01 $\mu$Ci tritium labeled phosphatidyl inositol bis-phosphate, 100 mM NaCl, 10 mM $CaCl_2$, and 5 mM 2-merceptoethanol. The sphingosine induced an approximately 2-fold increase in $V_{max}$, a decrease in calcium ion concentration required for optimal activity, and no effect on $K_M$ for substrate phosphatidylinositol bis-phosphate. Conversely, 10 μM lysocerebroside or 5 μM lysosphingomyelin induced a 60%±10% diminution in $V_{max}$, a 5-fold increase in calcium ion concentration required for optimal activity, and no change in $K_M$. These observations indicate that the lysosphingolipids affect the ability of calcium to activate phospholipase C and operate on a regulatory domain of the enzyme.

B. Monitoring Phospholipase C Activity in Intact Membranes

Physiologically active phospholipase C is present on the endofacial portion of the plasma membrane. A procedure for examining its activity in an intact membrane is provided. The neuronal membrane preparation described below is useful for determining lysosphingolipid effects on the phosphatidylinositol kinase and phospholipase C activities in intact membranes. One hundred Petri dishes of cultured cortical neurons were incubated overnight with 50 μCi [$^3$H]myo-inositol per mL of culture medium. Ten Petri dish-samples of cultured neurons (1×10$^8$ neurons; 23±2 mg protein, n=15) were pooled to produce 2.4±0.2 mg plasma membrane by the following procedure. The collected neurons were homogenized in 5 mL 0.32 M sucrose and centrifuged at 1000×g for 15 minutes. The supernatant was layered on top of 2 ml 1.2 M sucrose and centrifuged at 300,000×g for 20 minutes. The sedimented pellet was resuspended by sonication for 10 seconds in 50 mM Tris buffer (pH 7.4), containing 0.3 μM $CaCl_2$, 1 mM $MgCl_2$, and 0.01% ascorbic acid.

The suspended plasma membrane preparation was apportioned into 250 μl samples, each providing approximately 100 μg membrane protein. Sphingosine, psychosine, and lysosphingomyelin were added to each plasma membrane sample. The samples were held at room temperature for 3 hours, centrifuged at 300,000×g for 30 minutes, and the supernatant discarded. Samples were analyzed for lysosphingolipid loading (i.e., membrane lysosphingolipid content following exposure to exogenous sphingolipid) by fluorescence tagging. Table 2 provides the results of exposure of plasma membrane samples to 10 μM lysosphingolipids. Values are reported in pmoles lysosphingolipid/mg plasma membrane protein. Values obtained for isolated plasma membrane and intact neurons are compared.

Phospholipase C activity in plasma membrane samples in the presence of neuronal agonists is determined as follows. Replicate series of control and lysophingoolipid-loaded neuronal plasma membrane preparations pre-labelled with [$^3$H] myo-inositol are analyzed for phosphatidylinositol phosphate hydrolysis and inositol phosphate release. Membrane samples equivalent to 100 μg membrane protein in 250 μl buffer (50 mM Tris buffer (pH 7.4), containing 0.3 μM $CaCl_2$, 1 mM $MgCl_2$, 0.01% L-ascorbate, and 1 μM ATP) are incubated for 30 minutes at 37° C. in various concentrations of the neuronal agonists glutamate (0–100 μM), ibotenate, or quisqualate. Reactions are terminated by the addition of 1 ml ice-cold methanol to each sample followed by addition of 2 ml ice-cold chloroform. Diminution in phosphatidylinositol phosphates and release of inositol phosphates is estimated by thin layer chromatographic analysis, as described for phosphoinositidyl kinase activity analysis. Inositol phosphate release is plotted against μg lysosphingolipid per mg protein in the plasma membrane preparations and analyzed by Fisher's Least Squares Difference test. These data estimate lysosphingolipid modulation of phospholipase C activity in neuronal plasma membrane.

C. Monitoring Phosphatidylinositol Kinase Activity in Neuronal Plasma Membrane

Candidate compounds for use in modulating calcium ion levels in cells via $InsP_3$ production are evaluated in terms of the enzymatic process they affect. The enzymes phosphatidylinositol kinase and phospholipase C both transfer from the cytoplasm to the endofacial lipid bilayer of the plasma membrane for physiological activity. To control for any affects of phosphatidylinositol kinase activity in the plasma membrane preparations, a procedure for monitoring activity of this enzyme is provided herein along with a procedure for monitoring phospholipase C activity. Also, procedures for monitoring the activities of these enzymes in the presence of candidate compounds is provided below. In the following examples, naturally occurring lysosphingolipids are tested.

Phosphatidylinositol kinase (control) and lysosphingolipid-loaded neuronal plasma membrane samples are used to test for phosphatidylinositol kinase activity. The content of lysosphingolipids was increased (in the lysosphingolipid-loaded membrane) by exposure to exogenous lysosphingolipids and each sample contained the equivalent to 100 μg membrane protein. The membrane samples are pelleted and resuspended in 250 μl of buffer (50 mM Tris buffer (pH 7.4) containing 0.3 μM $CaCl_2$, 1 mM $MgCl_2$, and 0.01% ascorbic acid) by sonication for 5 seconds. They are then cooled to 0° C. and [$^{32}$P]-ATP (DuPont NEN, 1 TBeq/mmole) is added to 1μM. The samples are then incubated at 20° C. for 1 minute and placed in an ice bath to halt phosphorylation. The samples are vortexed with 1 ml ice-cold methanol:concentrated HCl (20:1, vol:vol). Two ml of ice-cold chloroform and 1 ml $H_2O$ are added with continuous vortexing. The samples are centrifuged at 2000×g for 10 minutes and the lower phase is drawn off.

TABLE 2

| Membrane Source | Lysosphingolipid 10 μmolar exposure | HOURS OF INCUBATION | | | | |
|---|---|---|---|---|---|---|
| | | 0 | 0.5 | 1.0 | 2.0 | 3.0 |
| Plasma Membrane Suspension | Sphingosine | 105 ± 5 | 113 ± 15 | 140 ± 15 | 165 ± 20 | 175 ± 25 |
| | Lysocerebroside (Psy) | 45 ± 5 | 75 ± 20 | 120 ± 15 | 180 ± 15 | 175 ± 20 |
| | Lysosphingomyelin | 5 ± 1 | 65 ± 15 | 110 ± 15 | 120 ± 10 | 145 ± 25 |
| Intact neurons | Sphingosine | 85 ± 15 | 85 ± 20 | 110 ± 15 | 105 ± 5 | 115 ± 15 |
| | Lysocerebroside (Psy) | 25 ± 5 | 35 ± 15 | 45 ± 10 | 80 ± 5 | 80 ± 5 |
| | lysosphingomyelin | 5 ± 1 | 8 ± 2 | 20 ± 5 | 45 ± 5 | 55 ± 15 |

Samples are analyzed for phosphatidylinositol and its mono- and bis-phosphate derivatives as a measure of phosphatidyl inositol kinase activity. Aliquots of each test sample, as well as reference standards of phosphatidylinositol and the mono- and bis-phosphate derivatives (Sigma Chemical Co., St. Louis, Mo.), are assayed, for example, by thin layer chromatography. Aliquots are chromatographed on silica gel G thin layer plates (Merck) that have been pre-soaked in 1% potassium oxalate dissolved in methanol:water (1:1, vol:vol), and dried at 120° C. for 1 hour. The plates are developed with the following mixture of solvents: chloroform:methanol:acetic acid:water at 40:15:12:13:8 (vol:vol). The developed plates are sprayed with Molybdenum Blue reagent (Sigma) which visualizes lipid-bound phosphoryl groups. Phosphatidylinositol, phosphatidylinositol mono-phosphate, and phosphatidylinositol bis-phosphate contents are analyzed relative to membrane protein by scanning in a BioRad Videodensitometer Model 620 coupled with the BioRad 1-D analyst program. Bands are then scraped and analyzed for radioactivity in a Beckman LS 5800 Scintillation Spectrometer.

Control and lysosphingolipid-loaded plasma membrane activities are compared by plotting phosphorylation labelling at $t_{1/2}$ (1 minute) against pg lysosphingolipid per mg membrane protein. Data are analyzed by Fisher's protected least significant difference test.

EXAMPLE 7

Methods of Modulating Inositol Trisphosphate Production in a Neuron in vivo for Treatment of a Neuronal Disorder Inositol trisphosphate production is modulated in vivo by administering a compound, such as a naturally occurring lysosphingolipid, to a mammal exhibiting symptoms of a neuronal disorder associated with aberrant $InsP_3$ production. Disorders associated with undesirable increases in $InsP_3$ production have been reviewed above and include acute brain hypoxia/ischemia and brain seizure, while chronic disorders include Alzheimer's disease, Huntington's disease, and amyotrophic lateral sclerosis. A disorder associated with an undesirable decrease in $InsP_3$ production is neuronal apoptosis or programmed cell death. Administration of the compound is performed under conditions such that symptoms of the disorder are controlled to a desirable level or alleviated.

A candidate compound for use in modulating $InsP_3$ production in vivo is screened by administering the candidate compound to an animal exhibiting a neuronal disorder associated with aberrant $InsP_3$ production. An example of such a test animal includes, but is not limited to, a DBA/2 mouse having audiogenic seizures (Thomsen et al., J. Neurochem. 62:2492–2495, 1994; incorporated by reference specifically to include a method of administering a neuroactive compound to an animal). Another in vivo screening model uses a gerbil which has surgically occluded common carotid arteries, which produces brain ischemia\anoxia (Matesik et al., J. Neurochem., 63:1012, 1994). Also incorporated by reference as in vivo screening models are the focally ischemic rat model (Zobrist et al., Stroke, 24:2002, 1994) and the Alzheimer's disease model adult mouse treated with beta-amyloid peptides (Hartmann et al., Biochem. Biophys. Res. Commmun., 194:1216, 1993).

Example VIII. In vivo Studies

Application of the specific metabotropic glutamate receptor agonist, quisqualate, to the lateral ventricle of the brain produces a dose-dependent behavioral response and loss of hippocampal neurons in rats. At a high dose (250 nmoles per animal), quisqualate produced severe convulsions and death. At a moderate dose (225 nmoles per animal), quisqualate produces moderate convulsions and death in 60% of animals tested. At a low dose (150 nmoles per animal), animals exhibit an increase in activity and teeth chattering. Seven days after application, both the moderate and high doses of quisqualate produce severe loss of neurons in the hippocampus. When these animals were pretreated with 125 nmoles of lysocerebroside (psychosine) or lysosphingomyelin, the behavioral and histological changes caused by quisqualate were absent. From this it was concluded that lysocerebroside or lysosphingomyelin are capable of preventing metabotropic glutamate excitotoxicity in vivo. In addition, no behavioral or neurotoxic effects were observed by doses of these compounds as high as 125 nmoles per animal.

The animals used in this experiment were male F344 rats (Charles River Breeding Laboratories). The animals were housed individually, exposed to a 12-hour light-dark cycle, and allowed free access to food and water. The animals weighed approximately 250 g at the beginning of each experiment and were weighed daily. In addition, the animals were habituated to handling before each experiment.

Before administering various compounds, the animals were anesthetized with sodium pentobarbital (50 mg/kg, i.p.) and positioned in a sterotaxic instrument. A 26 gauge cannula was inserted into the cerebral ventricle at the following co-ordinates: 1.0 mm posterior to bregma, 1.5 mm lateral to the midline, and 4.0 mm below the dorsal surface of the neocortex. Cannulas were capped and fixed in place with dental cement. One week after cannulation, 10 µl of each of the treatment drugs was infused, ICV (i.e. into the ventricals of the brain), via a micropump at a rate of 10 µl/min. For this procedure, the animals were lightly restrained and unanesthetized. Following administration of the compound, the infusion cannula remained in position for one minute, after which the permanent in situ cannula was capped.

The compounds administered were obtained from a commercial supplier (Sigma Chemical Co., St. Louis, Mo.) and dissolved in saline prior to injection. These compounds included quisqualate (injected at doses ranging from 100 nmole/10 µl to 1 µmole/10 µl), lysocerebroside, and lysophingomyelin (which were injected at doses of 25 nmoles/10 µl to 150 nmoles/10 µl ).

A. Histological Analysis

Seven days after the compounds were administered, animals were sacrificed by transcardial perfusion with neutralized, buffered 10% formalin-saline. Their brains were removed, post-fixed overnight in 10% formalin-saline, and sectioned along the coronal plane (into 50 µm thick sections) on a freezing microtome. The sections were stained with cresyl violet to determine the extent of cellular destruction.

A subset of the animals in each group was sacrificed by transcardial perfusion with 4% paraformldehyde. The brains of these animals were removed, post-fixed for 48 hours in 4% paraformaldehyde, placed in PBS, embedded in paraffin, and sectioned at room temperature into 6 µm thick sections along the coronal plane.

Figure 5A:
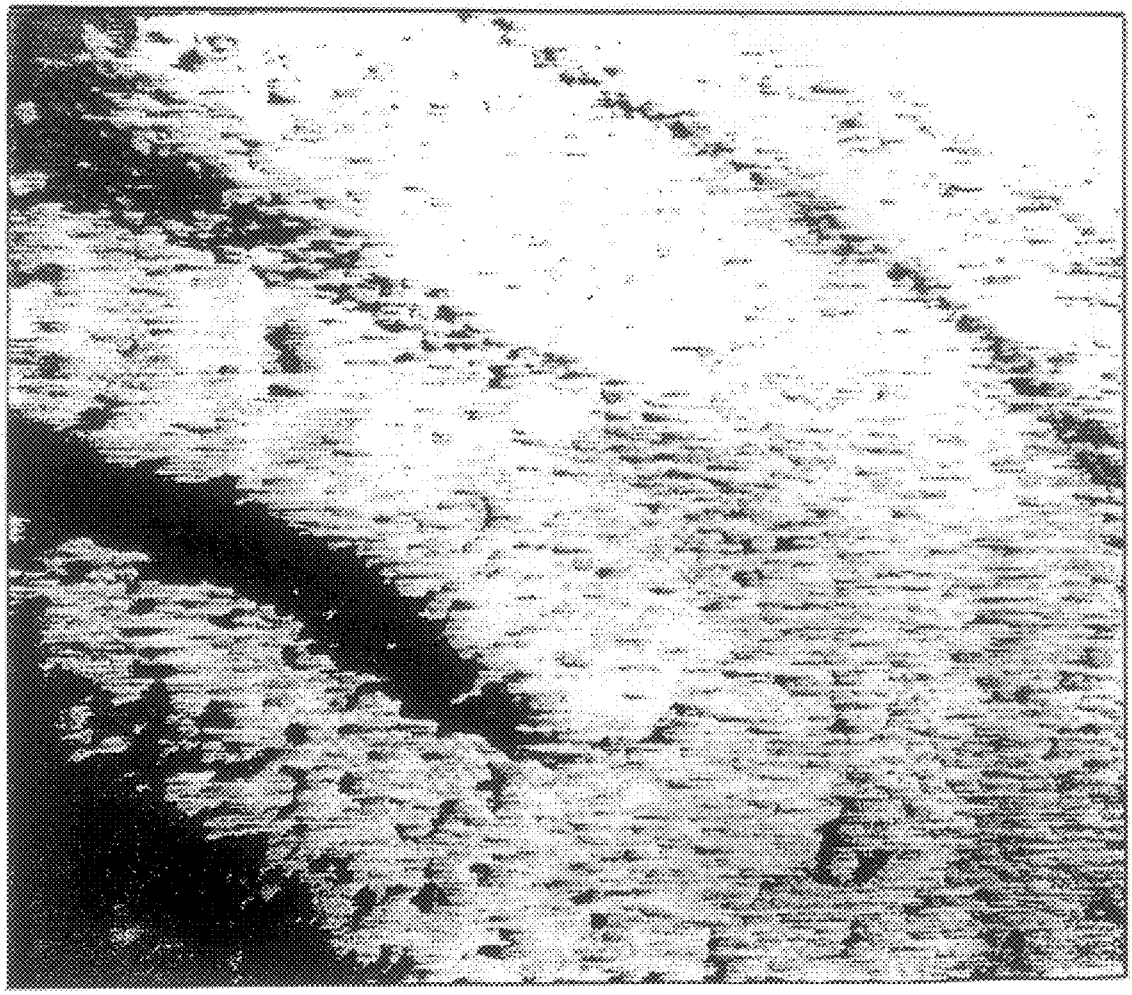
FIGS. 5A and 5B are scanned images at low (FIG. 5A) and high power magnification (FIG. 5B) of the CA1 region of the hippocampus 7 days after infusion of 225 nmoles quisqualate.
Figure 5B:
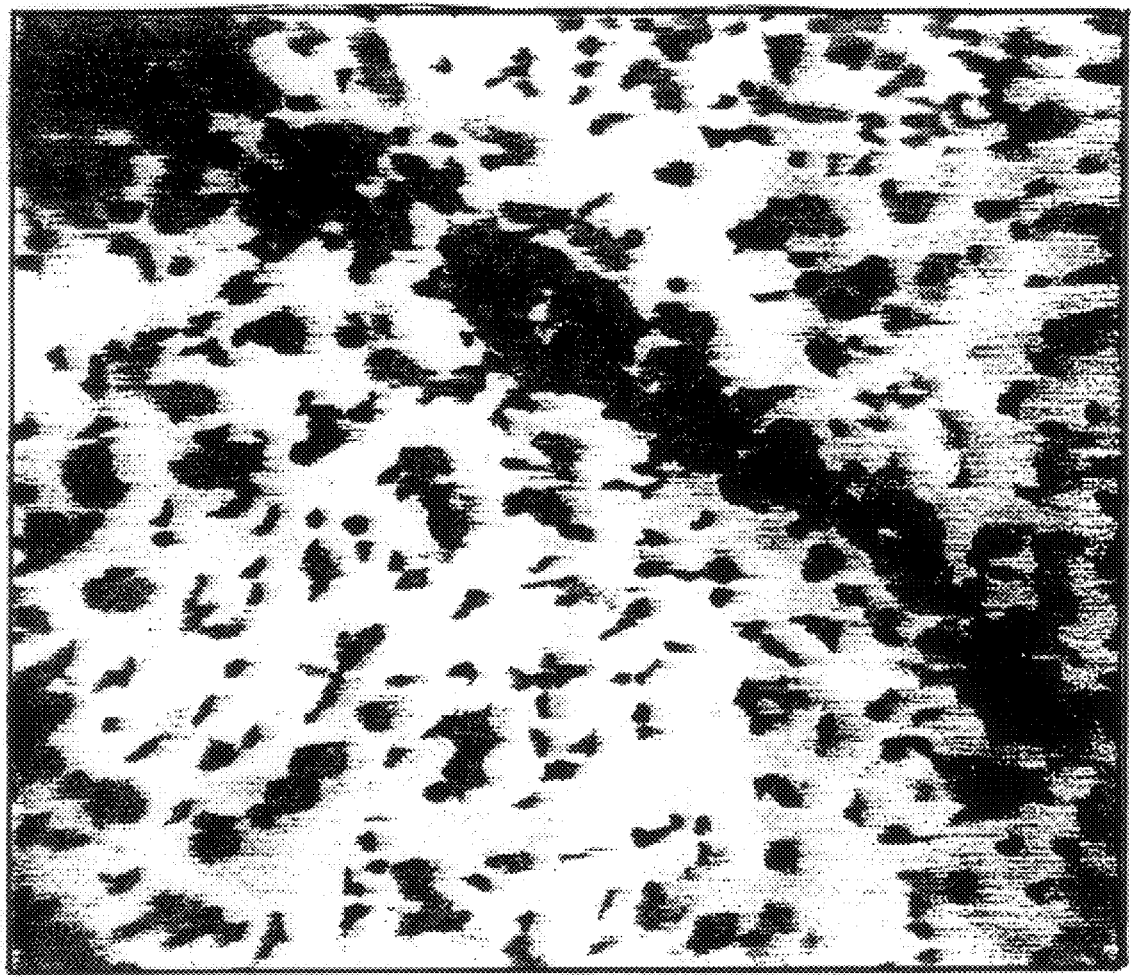
Figure 6A:
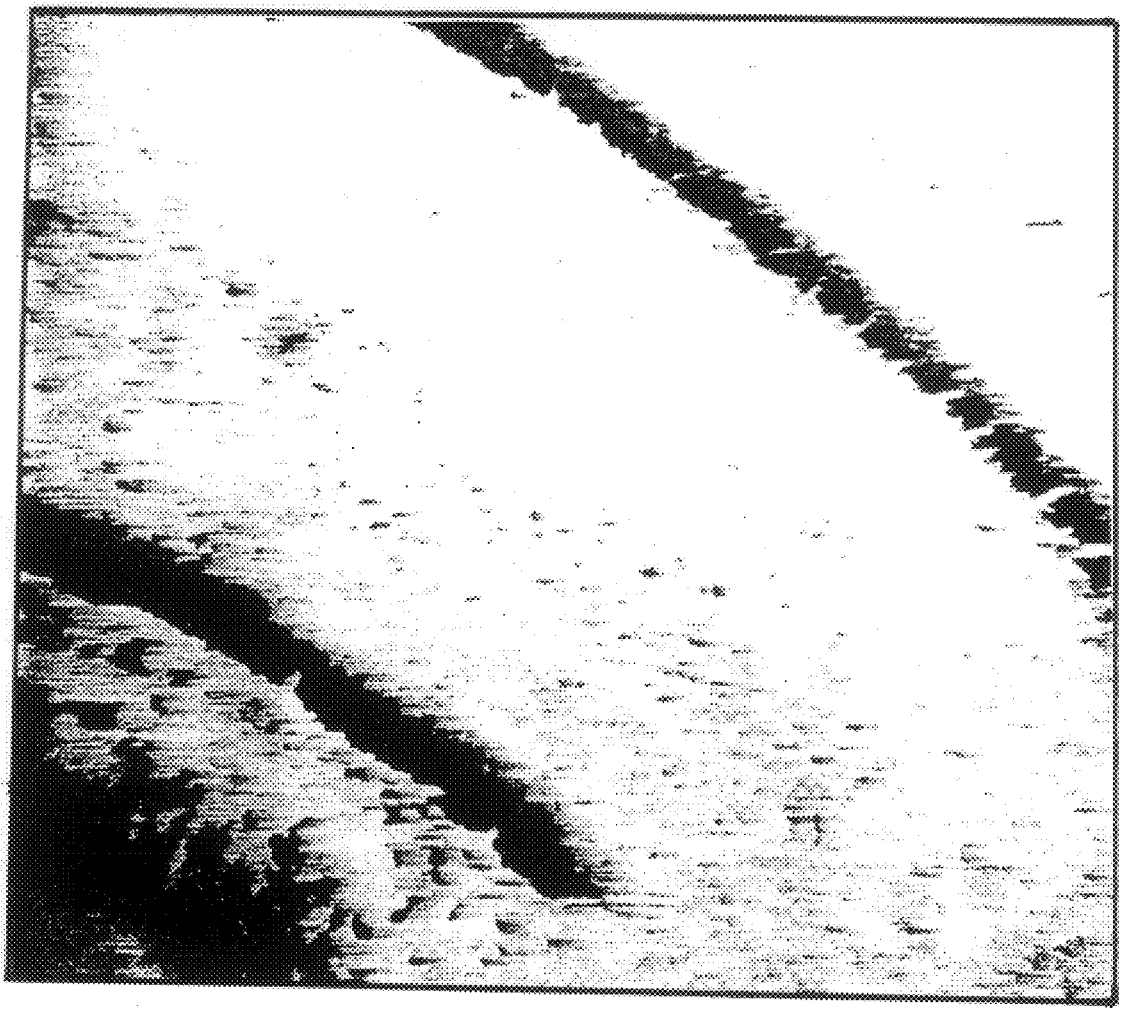
FIGS. 6A and 6B are scanned images at low (FIG. 6A) and high power magnification (FIG. 6B) of the CA1 region of the hippocampus 7 days after infusion of saline.
Figure 6B:
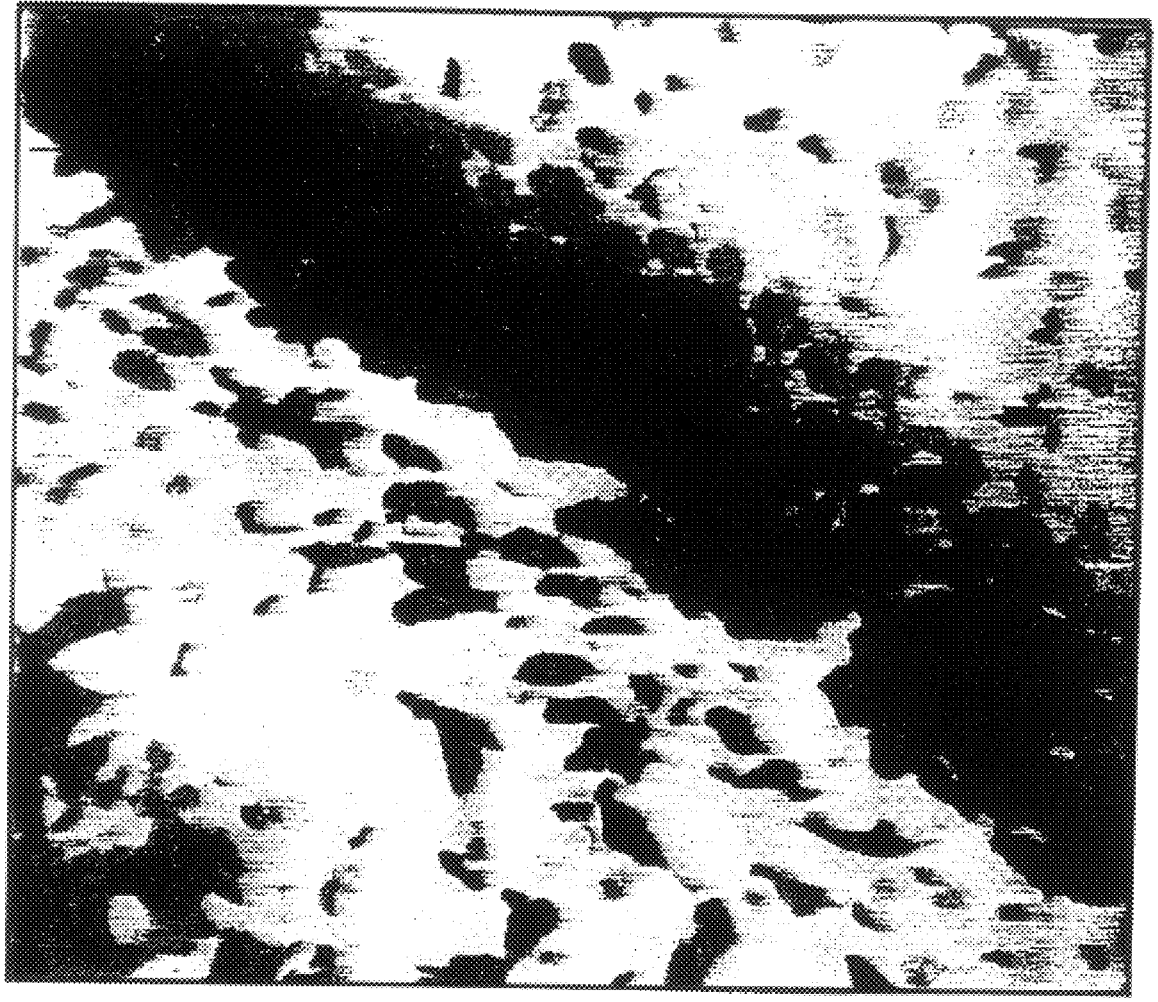
Figure 7A:
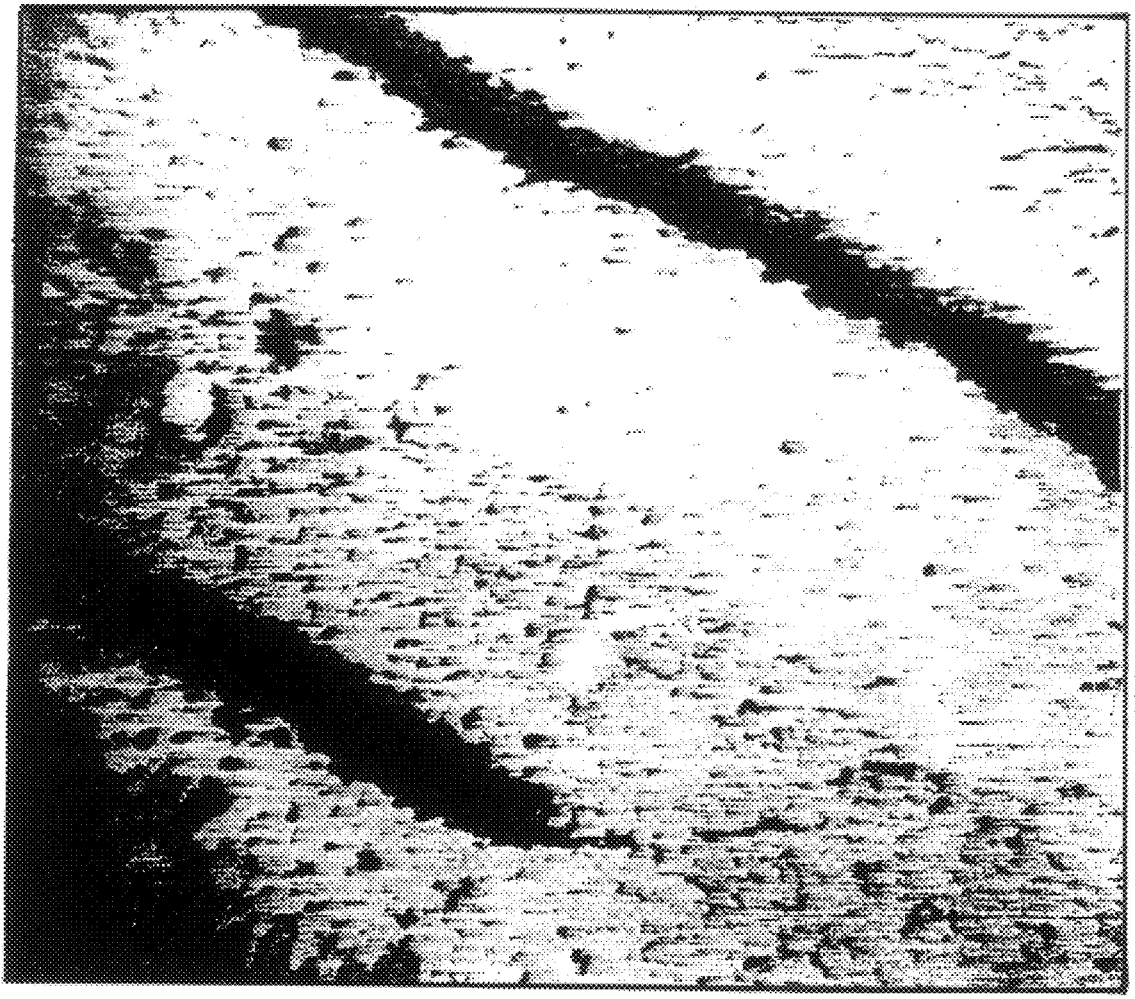
FIGS. 7A and 7B are scanned images at low (FIG. 7A) and high power magnification (FIG. 7B) of the CA1 region of the hippocampus seven days after treatment with 125 nmoles psychosine and subsequent exposure to 225 nmoles quisqualate.
Figure 7B:
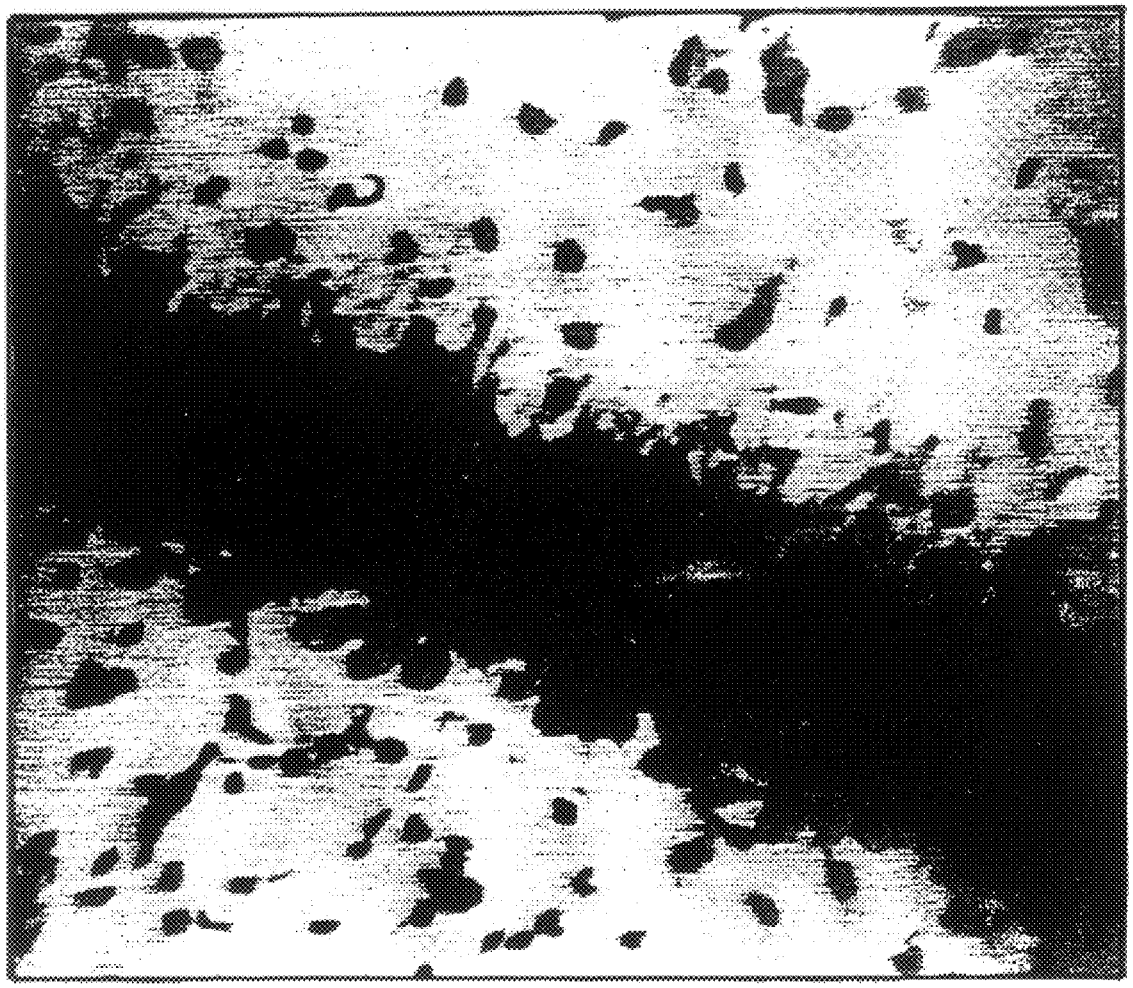

Given that high concentrations of metabotropic receptors are located in the hippocampus, and that the hippocampus is particularly vulnerable to the effects of a variety of insults including ischemia and hypoxia, this region was examined for evidence of neuronal degeneration due to glutamate excitotoxicity. Histological analysis of brain slices using cresyl violet staining confirm that quisqualate (225 nmoles) injected ICV produces a considerable loss of CA1 pyramidal neurons in the hippocampus (FIGS. 5A and 5B) compared to saline-injected controls (FIGS. 6A and 6B) and that pretreatment with psychosine (125 rinmoles) prevents the neuronal loss caused by quisqualate (FIGS. 7A and 7B).

B. Behavioral Analysis

Pilot studies identified several specific behavioral measures that could be used to indicate excessive activation of the metabotropic receptor (see Table 3). These behaviors include convulsions, spasms, teeth chattering, akinesia, and motor activity. The experiments that follow were based on an analysis of these behaviors over a two hour period after administration of the compounds of the invention. Behavioral observation was carried out by two trained observers, who worked independently of one another and who were blind to the experimental groups. The frequency of convulsions and spasms, and the duration of teeth chattering, akinesia and mobilizing was recorded continuously for 20 minutes prior to administration of the compound of the invention and for 2 hours after the treatment. Frequency and duration means were computed by subtracting pre-infusion means from post-infusion means.

Some of the experiments that were performed first were carried out to determine the amount of quisqualate required to produce behavioral and histological changes and the amount of lysosphingolipids that could effectively prevent or reverse these effects. Table 3 outlines the behavioral responses of rats to various doses of quisqualate (injected as described above) and the associated histological changes. The behaviors are listed as they occur chronologically. The limb clasp and reflex tests indicate the degree of decortication. A limb clasp or placement score of zero is normal, and a score of 3 is severely abnormal.

TABLE 3

| DOSE Quisqualate | BEHAVIOR | HISTOLOGICAL CHANGES |
| --- | --- | --- |
| 500 μmoles | vocalization | loss of neurons in the piriform and entorhinal cortex. CA1 and dentate gyrus regions of the hippocampus |
| 1 μmoles | severe repeated full body convulsions<br>severe scratching<br>severe teeth chattering<br>foaming at mouth<br>dead 5–15 mins in 100% cases | as above |
| 250 nmoles | vocalization<br>teeth chattering<br>scratching<br>localized spasms jerking/twitching<br>full body convulsions-severe/repeated<br>foaming at mouth<br>respiratory distress<br>abnormal placement and clasp reflex (3)<br>death in 75% of cases | as above |
| 225 nmoles | teeth chatter<br>hind leg paralysis<br>hyperactivity/walk in circles<br>full body convulsions - moderate<br>localized spasms twitching/jerking<br>episodic akinesia/tonic immobility<br>respiratory distress<br>foaming at mouth<br>abnormal placement and clasp reflex (1–2)<br>death in 60% of cases | loss of CA1 pyramidal neurons in the hippocampus |
| 200 nmoles | teeth chatter<br>occasional mild convulsions<br>hyperactivity - circle walking<br>episodic akinesia/tonic immobility<br>hind leg weakness<br>normal limb clasp and placement reflex (0) | as above |
| 150 nmoles | teeth chatter<br>localized twitches<br>mild hyperactivity walking in circles<br>hind leg weakness for 60 minutes<br>normal placement and clasp reflex (0) | none observed |

TABLE 3-continued

| DOSE Quisqualate | BEHAVIOR | HISTOLOGICAL CHANGES |
| --- | --- | --- |
| 100 nmoles | teeth chatter<br>mild scratching<br>hind leg weakness 60 minutes<br>normal placement and clasp reflex (0) | none observed |

The effective dose of quisqualate was determined to be 225 nmoles, that of lysocerebroside was determined to be 125 nmoles, and that of lysosphingomyelin was determined to be either 125 nmoles or 150 nmoles (the higher doses appeared to be more reliable in pilot testing).

The data shown in Table 4 represents the observations of pilot studies aimed at determining the effect (on behavior) of lysosphingolipids infused directly into the lateral ventricles of the brain 30 minutes prior to infusion of quisqualate.

TABLE 4

| DOSE | BEHAVIORAL RESPONSE |
| --- | --- |
| Psychosine 25 nmoles + Quisqualate 200 nmoles | Moderate convulsions, teeth chattering, akinesia and hyperactivity |
| Psychosine 50 nmoles + Quisqualate 200 nmoles | Moderate convulsions, teeth chattering, akinesia and hyperactivity |
| Psychosine 100 nmoles + Quisqualate 200 nmoles | Almost complete attenuation of Quisqualate response, some teeth chattering post-injection |
| Psychosine 125 nmoles + Quisqualate 200 nmoles | Complete attenuation of Quisqualate response |
| Psychosine 125 nmoles + Quisqualate 225 nmoles | Complete attenuation of Quisqualate response |
| Psychosine 100 nmoles + Quisqualate 250 nmoles | Moderate convulsions, teeth chattering, akinesia. Quisqualate markedly reduced compared to typical Quisqualate response at this dose. |
| Psychosine 150 nmoles + Quisqualate 250 nmoles | Almost complete attenuation of Quisqualate response. Psychosine produced short term sedation at this dose. |
| Lysosphingomyelin 100 nmoles + Quisqualate 225 nmoles | Almost complete attenuation of Quisqualate response, some teeth chattering post-injection and hyperactivity. |
| Lysosphingomyelin 150 nmoles + Quisqualate 225 nmoles | Complete attenuation of quisqualate response. Lysosphingomyelin produced mild sedation at this dose. |

The experiment began one week after ICV cannulation. Animals (n=6 per group) were randomly allocated to one of 8 treatment groups: (1) saline, (2) quisqualate at 225 nmoles, (3) psychosine at 125 nmoles, (4) lysosphingomyelin at 125 nmoles, (5) lysosphingomyelin at 150 nmoles, (6) quisqualate at 225 nmoles and psychosine at 125 nmoles, (7) quisqualate at 225 nmoles and lysosphingomyelin at 125 nmoles, and (8) quisqualate at 225 nmoles and lysosphingomyelin at 150 nmoles. Following the baseline observation period, animals received the first of two ICV infusions (all infusions were of a 10 μl volume that was administered over a 1 minute period). For the first five groups listed above, this consisted of saline (10 μl/minute), for the following 3 groups the infusions were psychosine at 125 nmoles, lysosphingomyelin at 125 nmoles, or Iysosphingomyelin at 150 nmoles, respectively. Thirty minutes later, all animals received the second infusion which, for the first five groups listed above, consisted of saline, quisqualate at 225 nmoles, psychosine at 125 nmoles, lysosphingomyelin at 125 mrnoles, and lysosphingomyelin at 150 nmoles respectively. The remaining three groups received infusions of quisqualate at 225 ramoles. Following the second infusion animals were returned to their cages, and observed continuously over the subsequent 2 hours.

Figure 8:
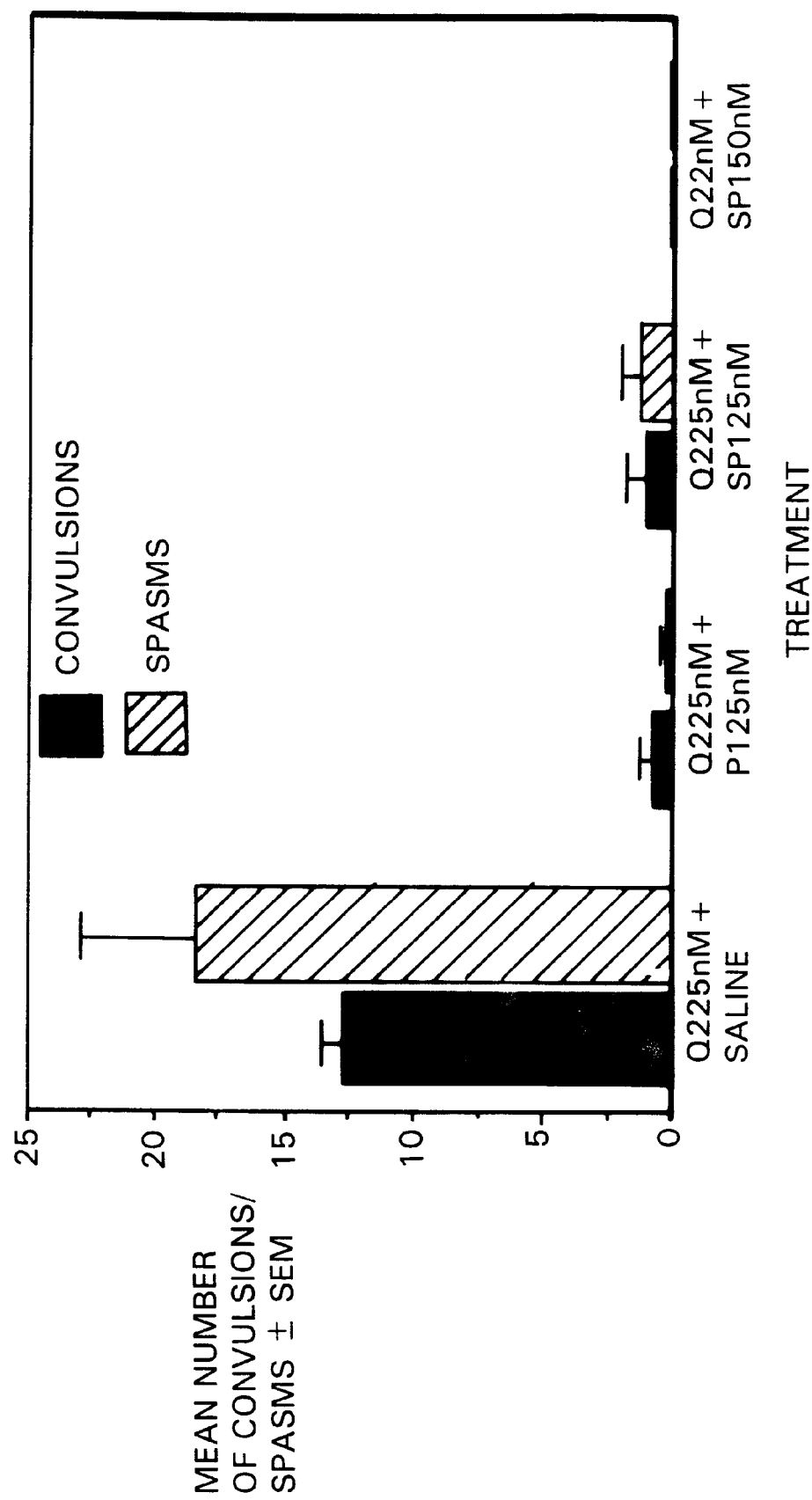
FIG. 8 is a bar graph illustrating the mean number of convulsions or spasms (±SEM) across four groups of treated animals. Q=quisqualate; P=psychosine; SP=lysosphingomyelin.

During the observation period, two behavioral analyses were carried out. The first on the frequency of spasms and convulsions, the second on the duration of teeth chattering, akinesia and motor activity. FIG. 8 illustrates the mean number of convulsions or spasms across 4 of the main treatment groups (quisqualate at 225 nmoles+saline; quisqualate at 225 nmoles+psychosine at 125 nmoles; quisqualate at 225 nmoles+lysosphingomyelin at 125 nmoles; and quisqualate at 225 nmoles+lysosphingomyelin at 150 nmoles). The remaining 4 control groups (saline; psychosine at 125 nmoles; and lysosphingomyelin at 125 nmoles and 150 nmoles) have not been illustrated, since animals in these treatment groups displayed no convulsant behavior. A two way ANOVA, group X response on the mean frequency of convulsions or spasms revealed a significant group effect ($F(7.24=9.75, p<.05)$). Multiple comparisons, using the Bonferroni adjustment, revealed that there were significantly ($p.<01$) more convulsions/spasms in the group injected with quisqualate alone at 225 nmoles compared to all other groups. Pretreatment with Psychosine (125 nmoles) or Lysosphingomyelin (125 nmoles and 150 nmoles) significantly ($p<01$) attenuated the number of convulsions or spasms, although there was no significant difference between the three treatment groups.

Figure 9:
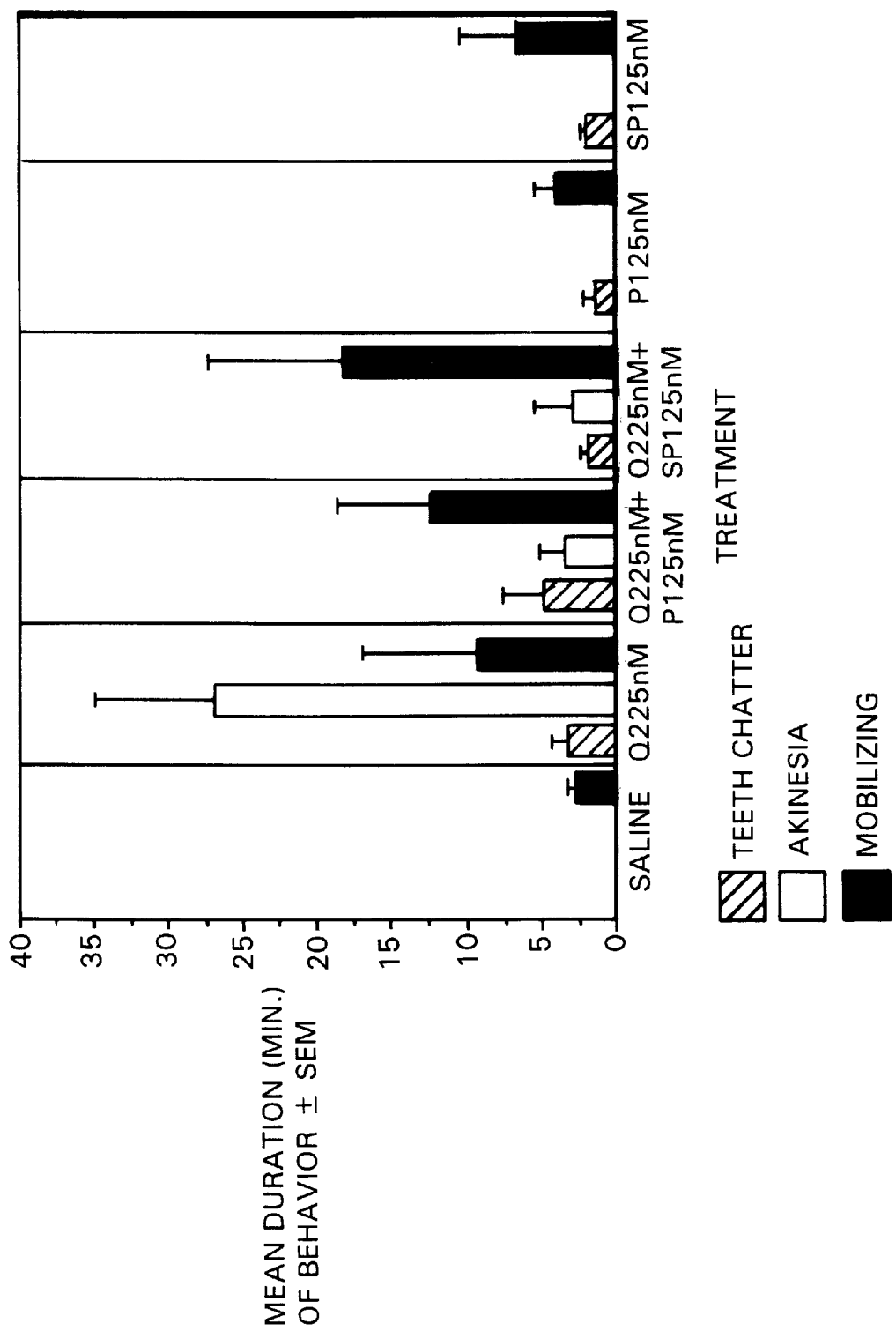
FIG. 9 is a bar graph illustrating the mean duration (in minutes) of three behaviors (±SEM): teeth chatter, akinesia, and mobilizing. Q=quisqualate; P=psychosine; SP=lysosphingomyelin.

The second analysis was carried out on the duration of teeth chattering, akinesia and mobilization. FIG. 9 illustrates the mean duration of each of these behaviors. A two way ANOVA, group X behavior, revealed a significant group effect ($F(7.34)=4.66, p=0.01$) and a significant behavior effect ($F(2.68)=3.98, p=0.023$). Multiple comparisons, using the Bonferroni adjustment, on the group effect revealed that animals injected with quisqualate alone spent significantly ($p<.01$) more time engaged in these behaviors than did animals injected with the lysophingolids alone (psychosine at 125 nmoles and lysophingomyelin at 125 nmoles and 150 nmoles) and animals injected with quisqualate 225 nmoles and lysophingomyelin 150 nmoles. Multiple comparisons on the behavior effect revealed that animals spent significantly ($p<.05$) more time mobilizing compared to engaging in teeth chatter.

Although the invention has been described with reference to the presently preferred embodiments, it should be understood that various modifications can be made without departing from the spirit of the invention.

What is claimed is:

1. A method of treating a mammal having or suspected of having brain anoxia, brain seizure activity, Alzheimer's Disease, Parkinson's Disease, Huntington's Disease, or amyotrophic lateral sclerosis, the method comprising administering to the mammal lysocerebroside or lysosphingomyelin.

2. A method of treating a mammal having or suspected of having brain anoxia, the method comprising administering to the mammal lysocerebroside or lysosphingomyelin.

3. A method of treating a mammal having or suspected of having brain seizure activity, the method comprising administering to the mammal lysocerebroside or lysosphingomyelin.

4. A method of treating a mammal having or suspected of having Alzheimer's Disease, method comprising administering to the mammal lysocerebroside or lysophingomyelin.

5. A method of treating a mammal having or suspected of having Parkinson's Disease, the method comprising administering to the mammal lysocerebroside or lysosphingomyelin.

6. A method of treating a mammal having or suspected of having Huntington's Disease, the method comprising administering to the mammal lysocerebroside or lysosphingomyelin.

7. A method of treating a mammal having or suspected of having amyotrophic lateral sclerosis, the method comprising administering to the mammal lysocerebroside or lysosphingomyelin.

* * * * *